US006455566B1

(12) United States Patent
Steffan et al.

(10) Patent No.: US 6,455,566 B1
(45) Date of Patent: Sep. 24, 2002

(54) SUBSTITUTED 1-ARYL-3-HETEROARYL-THIOUREAS (OR ISOTHIOUREAS) AS ANTIATHEROSCLEROTIC AGENTS

(75) Inventors: Robert J. Steffan, Langhorne, PA (US); Amedeo A. Failli, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/145,909

(22) Filed: Sep. 2, 1998

Related U.S. Application Data

(60) Provisional application No. 60/056,307, filed on Sep. 3, 1997, now abandoned.

(51) Int. Cl.[7] ..................... A61K 31/415; C07D 231/40
(52) U.S. Cl. ...................... 514/407; 548/371.7
(58) Field of Search .................. 548/371.4, 372.5, 548/373.1, 371.7; 514/407

(56) References Cited

U.S. PATENT DOCUMENTS

| 4,387,105 A | 6/1983 | DeVries et al. ............. 424/322 |
| 4,387,106 A | 6/1983 | DeVries et al. ............. 424/322 |
| 4,623,662 A | 11/1986 | DeVries ...................... 514/596 |
| 5,185,358 A | 2/1993 | Creswell et al. ............. 514/383 |
| 5,547,966 A | 8/1996 | Atwal et al. ................. 514/352 |

FOREIGN PATENT DOCUMENTS

| CA | 2072704 | 1/1993 |
| EP | A10656350 | 6/1995 |
| JP | 8301841 | 5/1995 |
| WO | A19315055 | 8/1993 |
| WO | A19640673 | 12/1996 |

OTHER PUBLICATIONS

Barr et al., *Am. J. Med.*, 11:480–493 (1951).
Gofman et al., *Circulation*, 34:679–697 (1966).
Miller and Miller, *Lancet*, 1:16–19 (1975).
Gordon et al., *Circulation*, 79:8–15 (1989).
Stampfer et al., *N. England J. Med.*, 325:373–381 (1991).
Badimon et al., *Lab. Invest.*, 60:455–461 (1989).
Miller et al., *Br. Med. J.*, 282:1741–1744 (1981).
Picardo et al., *Arteriosclerosis.*, 6:434–441 (1986).
Glomset, *J. Lipid Res.*, 9:155–167 (1968).
Glass et al., *J. Biol. Chem.*, 258:7161–7167 (1983).
MacKinnon et al., *J. Biol. Chem.*, 261:2548–2552 (1986).
Grow and Fried, *J. Biol. Chem.*, 253:8034–8041 (1978).
Lagocki and Scanu, *J. Biol. Chem.*, 255:3701–3706 (1980).
Schaefer et al., *J. Lipid Res..*, 23:1259–1273 (1982).
Cockerill et al., *Arterioscler., Thromb., Vasc. Biol.*, 15:1987–1994 (1995).

Primary Examiner—John M. Ford
(74) Attorney, Agent, or Firm—Michael R. Nagy

(57) ABSTRACT

Antiatherosclerotic agents are provided which are represented by Formulas I or II:

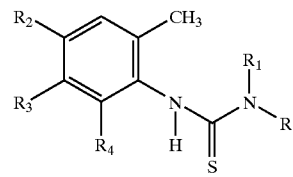

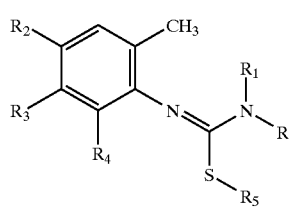

wherein
R is

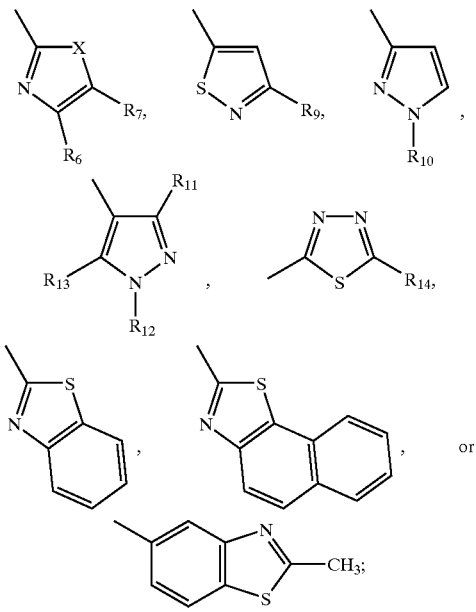

wherein $R_9$, $R_{10}$, $R_{11}$, $R_{12}$, $R_{13}$, and $R_{14}$ are each, independently, hydrogen or a lower alkyl of 1–6 carbon atoms;

$R_6$, and $R_7$ are each, independently, hydrogen, lower alkyl of 1–6 carbon atoms, or $CH_2COOR_8$, where $R_8$ is a lower alkyl of 1–6 carbon atoms; and X is O or S;

$R_1$ is hydrogen or a lower alkyl of 1–6 carbon atoms;

$R_2$, $R_3$, and $R_4$ are each, independently, hydrogen or halogen; and $R_5$ is a lower alkyl of 1–6 carbon atoms;

or a pharmaceutically acceptable salt thereof.

9 Claims, No Drawings

SUBSTITUTED 1-ARYL-3-HETEROARYL-THIOUREAS (OR ISOTHIOUREAS) AS ANTIATHEROSCLEROTIC AGENTS

CROSS REFERENCE TO RELATED APPLICATIONS

This application claims the benefit of U.S. Provisional Application No. 60/056,307 filed Sep. 3, 1997, now abandoned.

FIELD OF THE INVENTION

This invention is directed to antiatherosclerotic agents and more specifically to compounds, compositions and methods useful for elevating HDL cholesterol concentration which may be useful in the treatment of atherosclerosis and related conditions, such as dyslipoproteinemias and coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.*, 11 (1951) 480–483; Gofman et al. *Circulation*, 34 (1966), 679–697; Miller and Miller, *Lancet*, 1 (1975), 16–19; Gordon et al., *Circulation*, 79 (1989), 8–15; Stampfer et al., *N. Engl. J. Med.*, 325 (1991), 373–381; Badimon et al., *Lab. Invest.*, 60 (1989), 455–461). Atherosclerosis is the process of accumulation of cholesterol within the arterial wall which results in the occlusion, or stenosis, of coronary and cerebral arterial vessels and subsequent myocardial infarction and stroke. Angiographic studies have shown that elevated levels of some HDL particles in humans appear to be correlated to a decreased number of sites of stenosis in the coronary arteries of humans (Miller et al., *Br. Med. J.*, 282 (1981), 1741–1744).

There are several mechanisms by which HDL may protect against the progression of atherosclerosis. Studies in vitro have shown that HDL is capable of removing cholesterol from cells (Picardo et al., *Arteriosclerosis*, 6 (1986), 434–441). Data of this nature suggest that one antiatherogenic property of HDL may lie in its ability to deplete tissue of excess free cholesterol and eventually lead to the delivery of this cholesterol to the liver (Glomset, *J. Lipi Res.*, 9 (1968), 155–167). This has been supported by experiments showing efficient transfer of cholesterol from HDL to the liver (Glass et al., *J. Biol. Chem.*, 258 (1983), 7161–7167; McKinnon et al., *J. Biol. Chem.*, 261 (1986), 2548–2552). In addition, HDL may serve as a reservoir in the circulation for apoproteins necessary for the rapid metabolism of triglyceride-rich lipoproteins (Grow and Fried, *J. Biol. Chem.*, 253, (1978), 1834–1841; Lagocki and Scanu, *J. Biol. Chem.*, 255 (1980), 3701–3706; Schaefer et al., *J. Lipid Res.*, 23 (1982), 1259–1273). More recently, as a possible mechanism for protection against the development of atherosclerosis, Cockerill et. al. (*Arterioscler., Thromb., Vasc., Biol*, 15, (1995), 1987–1994) have demonstrated that plasma HDL inhibit the cytokine-induced expression of endothelial cell adhesion molecules (VCAM-1 and ICAM-1) in a concentration dependent and cell specific manner. Accordingly, it is believed that agents which increase HDL cholesterol concentration would be of utility as anti-atherosclerotic agents, useful particularly in the treatment. of dyslipoproteinimias and coronary heart disease.

Ureas, thioureas and derivatives thereof are known to be useful for the treatment of various conditions. For example, the use of urea and thiourea derivatives as tyrosine kinase inhibitors, to inhibit cell proliferation and differentiation in the treatment of cancer is disclosed in WO 9640673-A1. The use of [(alkoxy) pyridinyl] amino derivatives to inhibit the secretion of gastric acid is disclosed in WO-9315055. N-phenyl thiourea derivatives and their use in the treatment of atherosclerosis is disclosed in CA-2072704. The use of bis-aryl ureas and related compounds as cardiovascular agents is disclosed in CA-2132771, while the administration of ureas and thioureas for the treatment of ischaemia, asthma, Parkinson disease, epilepsy, and urinary incontinence is disclosed in U.S. Pat. No. 5,547,966. Substituted thioureas and isothioureas are also disclosed in U.S. Pat. No. 5,185,358.

The treatment of atherosclerosis with certain ureas, thioureas and derivatives thereof has been suggested in Japanese Patent 83-01841 (the use of ureas and thioureas as inhibitors of squalene epoxidase); U.S. Pat. No. 4,623,662 (the use of certain urea and thiourea compounds to lower serum lipids in warm-blooded animals); and U.S. Pat. Nos. 4,387,105 and 4,387,106 (the use of di(aralkyl) ureas and di(aralkyl) thioureas to inhibit fatty acyl CoA: cholesterol acyl transferase). However, the treatment of atherosclerosis, and the related cardiovascular disease and dyslipoproteinemias, through the elevation of serum HDL cholesterol concentrations with the present urea and thiourea derivatives, has heretofore not been recognized.

SUMMARY OF THE INVENTION

The present invention relates to antiatherosclerotic agents comprising 1-aryl-3-heteroaryl-thioureas and 1-aryl-3-heteroaryl-isothioureas represented by formulas I and II:

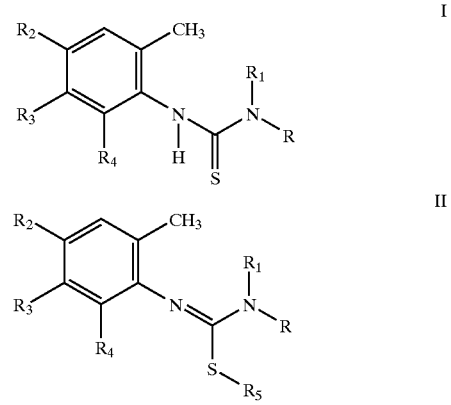

wherein

R is

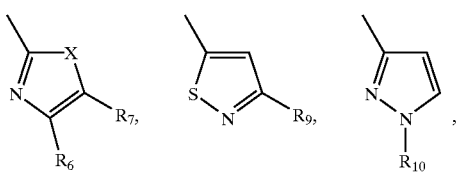

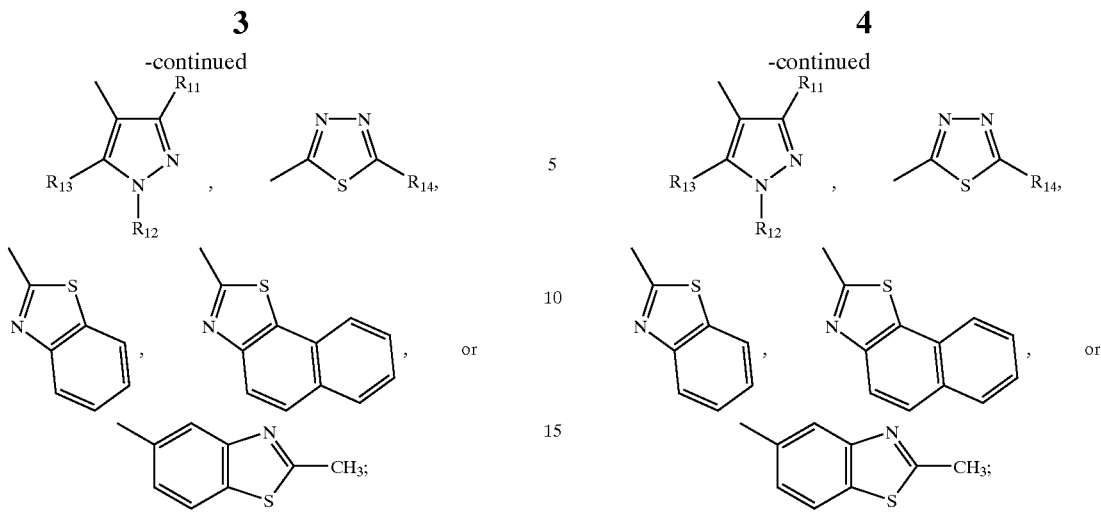

wherein $R_9$, $R_{10}$, $R_{11}$, $R_{12}$, $R_{13}$, and $R_{14}$ are each, independently, hydrogen or a lower alkyl of 1–6 carbon atoms;

$R_6$, and $R_7$ are each, independently, hydrogen, lower alkyl of 1–6 carbon atoms, or $CH_2COOR_8$, where $R_8$ is a lower alkyl of 1–6 carbon atoms; and X=O or S;

$R_1$ is hydrogen or a lower alkyl of 1–6 carbon atoms;

$R_2$, $R_3$, and $R_4$ are each, independently, hydrogen or halogen; and $R_5$ is a lower alkyl of 1–6 carbon atoms;

or a pharmaceutically acceptable salt thereof.

The present invention is further directed to methods of elevating the HDL concentration and treating atherosclerosis and related coronary heart disease and dyslipoproteinemias in a mammal in need thereof, comprising administering to the mammal an effective amount of the antiatherosclerotic agents of formulas I and II:

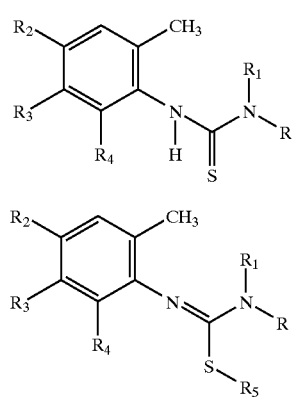

wherein

R is

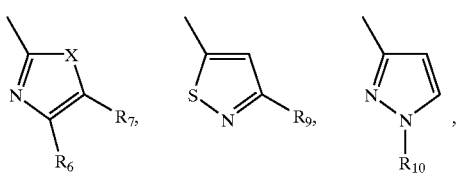

wherein $R_9$, $R_{10}$, $R_{11}$, $R_{12}$, $R_{13}$, and $R_{14}$ are each, independently, hydrogen or a lower alkyl of 1–6 carbon atoms;

$R_6$, and $R_7$ are each, independently, hydrogen, lower alkyl of 1–6 carbon atoms, or $CH_2COOR_8$, where $R_8$ is a lower alkyl of 1–6 carbon atoms; and X is O or S;

$R_1$ is hydrogen or a lower alkyl of 1–6 carbon atoms;

$R_2$, $R_3$, and $R_4$ are each, independently, hydrogen or halogen; and $R_5$ is a lower alkyl of 1–6 carbon atoms;

or a pharmaceutically acceptable salt thereof.

DETAILED DESCRIPTION OF THE INVENTION

Preferably, the antiatherosclerotic agents of the present invention are those represented by formulas I and II where:

R is

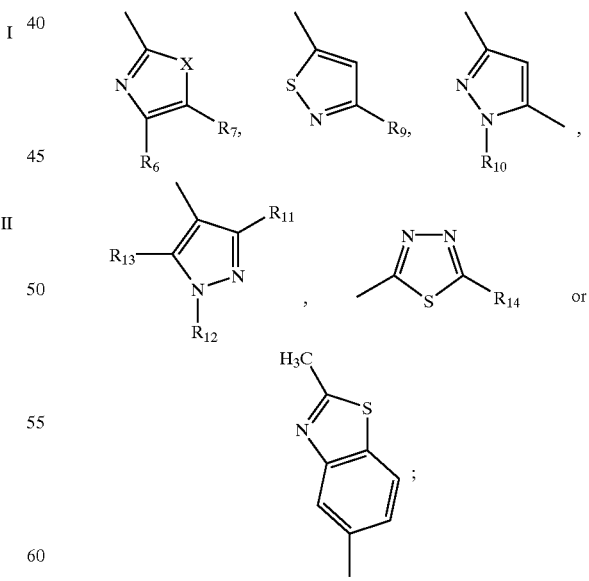

wherein:

$R_9$, $R_{10}$, $R_{11}$, $R_{12}$, $R_{13}$, and $R_{14}$ are each, independently, hydrogen or lower alkyl of 1 to 6 carbon atoms;

$R_6$ and $R_7$ are, each independently, lower alkyl of 1 to 6 carbon atoms; and X is O or S;

R₁ is hydrogen;

R₂, R₃, and R₄ are each, independently, hydrogen or halogen; and

R₅ is a lower alkyl of 1 to 6 carbon atoms;

or a pharmaceutically acceptable salt thereof.

As used in this invention, the term "lower alkyl" includes both straight chain as well as branched moieties. The terms "halo" or "halogen" includes fluorine, chlorine, bromine, and iodine.

The compounds of Formula I are known to be unstable to salt formation. Accordingly, the expression "pharmaceutically acceptable salts" as used herein should be construed as applying only to the compounds of Formula II. The pharmaceutically acceptable salts of the present compounds include those derived from organic and inorganic acids, including, but not limited to, acetic, lactic, citric, tartaric, succinic, fumaric, maleic, malonic, malic, hydrochloric, hydrobromic, phosphoric, nitric, sulfuric, methane sulfonic, toluene sulfonic and similarly known acceptable acids.

The most preferred compounds according to this invention are:

1-(5-Chloro-2-methyl-phenyl)-3-(thiazol-2-yl)-thiourea;

1-(5-Chloro-2-methyl-phenyl)-3-(4-methyl-oxazol-2-yl)-thiourea;

1-(5-Chloro-2-methyl-phenyl)-3-(5-methyl-[1,3,4]thiadiazol-2-yl)-thiourea;

1-(5-Chloro-2-methyl-phenyl)-3-(1 H-pyrazol-3-yl)-thiourea;

1-(5-Chloro-2-methyl-phenyl)-3-(1,3,5-trimethyl-1H-pyrazol-4-yl)-thiourea;

1-(5-Chloro-2-methyl-phenyl)-3-(4-methyl-thiazol-2-yl)-thiourea;

1-(5-Chloro-2-methyl-phenyl)-3-(4,5-dimethyl-thiazol-2-yl)-thiourea;

1-(5-Chloro-2-methyl-phenyl)-3-(3-methyl-isothiazol-5-yl)-thiourea;

1-(5-Chloro-2-methyl-phenyl)-3-(2-methyl-benzothiazolyl-5-yl)-thiourea;

1-(5-Chloro-2-methyl-phenyl)-3-(5-ethyl-[1,3,4]thiadiazol-2-yl)-thiourea;

1-(2-Chloro-6-methyl-phenyl)-3-(1,3,5-trimethyl-1H-pyrazol-4-yl)-thiourea;

1-(4-Chloro-2-methyl-phenyl)-3-(1,3,5-trimethyl-1H-pyrazol-4-yl)-thiourea;

1-(4-Chloro-2-methyl-phenyl)-3-(4-methyl-oxazol-2-yl)-thiourea;

1-(2-Chloro-6-methyl-phenyl)-3-(4-methyl-oxazol-2-yl)-thiourea;

3-(5-Chloro-2-methyl-phenyl)-1-ethyl-1-(1,3,5-trimethyl-1H-pyrazol-4-yl)-thiourea;

(E)-1-(5-Chloro-2-methyl-phenyl)-2-methyl-3-(1,3,5-trimethyl-1H-pyrazol-4-yl)-isothiourea; and 3-(5-Chloro-2-methyl-phenyl)-1-ethyl-2-methyl-1-(1,3,5-trimethyl-1H-pyrazol-4-yl)-isothiourea.

The 1-aryl-3-heteroaryl-thioureas of the present invention may be prepared by the reaction of an appropriately substituted aryl-isothiocyanate with a substituted amino heterocycle (see, e.g., J. March, *Advanced Organic Chemistry*, 3rd Ed., Wiley-Interscience, NY, page 802) as shown in scheme 1

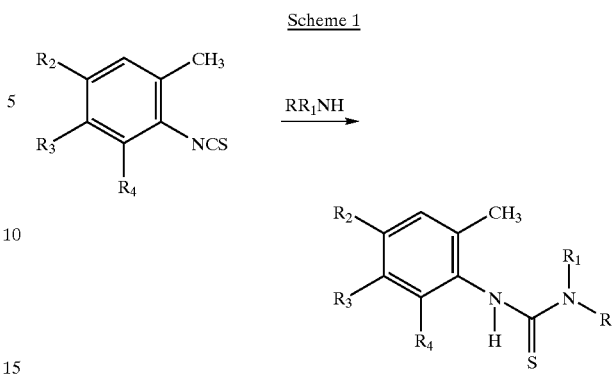

Scheme 1 wherein R, R₁, R₂, R₃, and R₄ are as described above for formula I.

The substituted heterocyclic amine starting materials are either commercially available, known in the art or can be prepared by procedures analogous to those in the literature for known heterocycles (see Katritzky, *Handbook of Heterocyclic Chemistry*, Pergamon Press, NY, 416–428 and 468–469, (1985)). Primary heterocyclic amines can be functionalized to secondary amines in a manner known to those skilled in the art, such as described below in Example 21.

The appropriately substituted aryl isothiocyanates starting materials are either commercially available, known in the art or can be prepared by procedures analogous to those in the literature.

The substituted 1-aryl-3-heteroaryl-isothioureas of the present invention may be prepared from 1-aryl-3-heteroaryl-thioureas under S-alkylating conditions as described e.g., in Rassmussen, C. R. et al, *Synthesis* 460, (1988) as shown scheme 2:

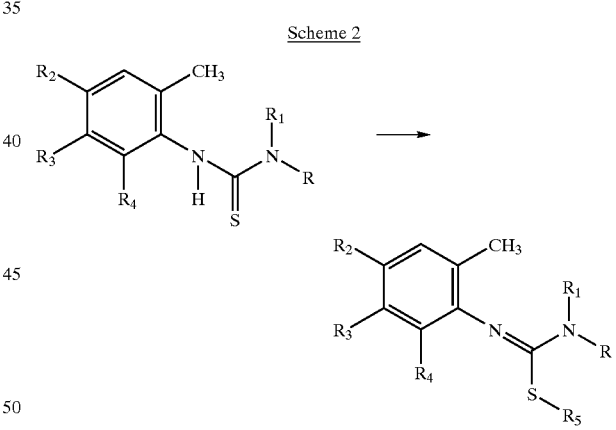

Scheme 2 wherein R, R₁, R₂, R₃, R₄ and R₅ are as described above for formula II.

Representative compounds according to the present invention were evaluated in an in vivo standard pharmacological test procedure which measured the ability of the compounds to elevate HDL cholesterol levels. The following describes the procedure used and results obtained. Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance was administered to a group of six rats fed the same diet with the test diet mixed in as 0.005–0.1% of the total diet. Body weight and food consumption were recorded prior to diet administration and at termination. The test substances were administered at a dosage of 100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzene sulfonate in a pH 6.5 buffer. In the reaction, cholesterol was oxidized to produce hydrogen peroxide which was used to form a quinoneimine dye. The concentration of dye formed was measured spectrophotometrically by absorbance at 490 nm after incubation at 25° C. for 30 minutes. The concentration of cholesterol was determined for each serum sample relative to a commercial standard from Sigma.

HDL cholesterol concentrations in serum were determined by separation of lipoprotein classes by fast protein liquid chromatography (FPLC) by a modification of the method of Kieft et al., *J. Lipid Res.*, 32 (1991), 859–866. Using this methodology, 25 mL of serum was injected onto Superose 12 and Superose 6 (available from Pharmacia), in series, with a column buffer of 0.05 M Tris (2-amino-2-hydroxymethyl-1,3-propanediol) and 0.15 M sodium chloride at a flow rate of 0.5 mL/min. The eluted sample was mixed on line with Boehringer-Mannheim cholesterol reagent pumped at 0.2 mL/min. The combined eluents were mixed and incubated on line through a knitted coil (available from Applied Biosciences) maintained at a temperature of 45° C. The eluent was monitored by measuring absorbance at 490 nm and gave a continous absorbance signal proportional to the cholesterol concentration. The relative concentration for each lipoprotein class was calculated as the percent of total absorbance. HDL cholesterol concentration in serum, was calculated as the percent of total cholesterol as determined by FPLC multiplied by the total serum choleterol concentration.

Test compounds were administered at a dose of 100 mg/kg for 8 days. The increase in serum concentrations of HDL cholesterol are summarized in Table 1.

TABLE 1

| Example Number | HDL Cholesterol Level Increase (%) |
|---|---|
| 1 | 65 |
| 2 | 6 |
| 3 | 0.3 |
| 4 | 158 |
| 5 | 69 |
| 6 | −11 |
| 7 | 97 |
| 8 | 110 |
| 9 | 79 |
| 10 | 41 |
| 11 | 2 |
| 12 | 134 |
| 13 | 36 |
| 14 | 90 |
| 15 | 58 |
| 16 | 104 |
| 17 | 134 |
| 18 | 193 |
| 19 | 79 |
| 20 | 35 |
| 21 | 29 |

The results set forth in Table I demonstrate that the compounds of the present invention are useful in raising the concentration of HDL cholesterol, and are therefore, useful for treating or inhibiting atherosclerosis, related cardiovascular disease, or dyslipoproteinemias, and for improving the HDL/LDL cholesterol ratio. Moreover, in light of their ability to elevate HDL cholesterol concentrations, the present compounds are useful in treating several metabolic conditions associated with low concentrations of HDL, such as low HDL-cholesterol levels in the absence of dyslipidemia, metabolic syndrome, non-insulin dependent diabetes mellitus (NIDDM), familial combined hyperlipidemia, familial hypertriglyceridemia, and dyslipidemia in peripheral vascular disease (PVD).

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs. The compounds of the present invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the present compounds are in unit dosage form, e.g. as tablets or capsules. In such form, the compositions are sub-divided in unit doses containing appropriate quantities of the active ingredient. The unit dosage forms can be packaged compositions, for example packeted powders, vials, ampoules, prefilled syringes or sachets containing liquids. The unit dosage form may also be, for example, a capsule or tablet itself, or it can be the appropriate number of any such compositions in package form.

The therapeutically effective amount of the compounds of this invention that is administered and the dosage regimen depends on a variety of factors, including the weight, age, sex, medical condition of the subject, the severity of the disease, the route and frequency of administration, and the specific compound employed, and thus may vary widely. However, it is believed that the pharmaceutical compositions may contain the present compounds in the range of about 0.1 to about 2000 mg, preferably in the range of about 0.5 to about 500 mg and most preferably between about 1 and about 100 mg. Projected daily dosages of active compound are about 0.01 to about 100 mg/kg body weight. The daily dose can be conveniently administered two to four times per day.

The following non-limiting examples illustrate the preparation of representative compounds of the present invention.

The 1-aryl-3-heteroaryl-thioureas of Examples 1–19 were prepared from substituted phenyl isothiocyanates by one of the following methods as indicated:

Method A: A solution (0.5 molar) of the substituted phenyl isothiocyanate and an equimolar amount of the heterocyclic amine in ethyl acetate was heated at reflux for 1 hour. Upon cooling, the solids formed were filtered, washed with $Et_2O$ and dried.

Method B: A solution (0.5 molar) of the substituted phenyl isothiocyanate and an equimolar amount of the heterocyclic amine in ethyl acetate was stirred overnight at ambient temperature. The solids formed were filtered and washed with $Et_2O$, and dried.

Method C: An equimolar mixture of the substituted phenyl isothiocyanate and the heterocyclic amine were heated neat at 75–125° C. for 2 hours. EtOH was added and the mixture was heated at reflux for 1 hour. When cold the solids formed were filtered, washed with $Et_2O$, and dried.

Method D: A solution (0.5 molar) of the substituted phenyl isothiocyanate and an equimolar amount of the heterocyclic amine in dioxane was heated at reflux overnight The reaction mixture was concentrated in vacuo to provide residual solids which were washed with $Et_2O$ and dried.

EXAMPLE 1

1-(5-Chloro-2-methyl-phenyl)-3-(thiazol-2-yl)-thiourea

Prepared using Method C from 3.0 g (16.3 mmol) of 5-chloro-2-methyl-phenyl isothiocyanate and 1.7 g (16.3 mmol) of 2-amino-thiazole to give 3.58 g of title compound as a beige solid, m.p. 197–198° C. (77% yield).

NMR (DMSO-$d_6$, 400 MHz): 2.19 (s, 3H, ArCH$_3$), 7.04 (broad s, 1H, ArH), 7.19 (dd, 1H, ArH), 7.22 (d, 1H, ArH), 7.41 (d, 1H, ArH), 7.44 (broad, 1H, ArH), 10.4 (broad, 1H, NH), 12.25 (broad, 1H, NH). MS [EI, m/z]: 283 [M]$^+$, 198,141, 100 [b.p.]; Anal. Calc'd. for $C_{11}H_{10}ClN_3S_2$+0.3 mol $H_2O$: C, 45.68; H, 3.69; N, 14.53; Found: C, 45.49; H, 3.33; N, 14.53.

EXAMPLE 2

1-(Benzothiazol-2-yl)-3-(5-chloro-2-methyl-phenyl)-thiourea

Prepared using Method A from 5.0 g (27.2 mmol) of 5-chloro-2-methyl-phenyl isothiocyanate and 3.90 g (26 mmol) of 2-aminobenzothiazole to give 2.7 g of title compound as a white fluffy solid (30% yield).

NMR (DMSO-$d_6$, 400 MHz): 2.223 (s, 3H, ArCH$_3$), 7.25 (m, 3H, ArH), 7.40 (t, 1H, ArH), 7.55 (broad s, 2H, ArH), 7.85 (broad, 1H, ArH). Multiple NH at 10.05, 11.2, 12.35, 12.9 indicate a mixture of rotamers. MS [EI, m/z]: 333 [M]$^+$, 150 [b.p.]; Anal. Calc'd. for $C_{15}H_{12}ClN_3S_2$: C, 53.96; H, 3.62; N, 12.59 Found: C, 54.09; H, 3.48; N, 12.54.

EXAMPLE 3

1-(5-Chloro-2-methyl-phenyl)-3-(naphtho[2,1-d]thiazol-2-yl)-thiourea

Prepared using Method A from 5.0 g (27.2 mmol) of 5-chloro-2-methyl-phenyl isothiocyanate and 5.0 g (25 mmol) of 2-amino-naptho[2,1-d]thiazole to give 2.1 g of title compound as an off-white solid, (21% yield).

NMR (DMSO-$d_6$, 400 MHz): 2.27 (s, 3H, ArCH$_3$), 7.34 (m, 2H, ArH), 7.64 (m, 3H, ArH), 7.82 (d, 1H, ArH), 8.02 (d, 2H, ArH), 8.51 (m, 1H, ArH), 10.8 (broad, 1H, NH), 12.42 (broad, 1H, NH). MS [EI, m/z]: 383 [M]$^+$, 349, 242, 200 [b.p.]; Anal. Calc'd. for $C_{19}H_{14}ClN_3S_2$: C, 59.44; H, 3.68; N, 10.94 Found: C, 59.26; H, 3.44; N, 10.95.

EXAMPLE 4

1-(5-Chloro-2-methyl-phenyl)-3-(4-methyl-oxazol-2-yl)-thiourea

Prepared using Method A from 10.0 g (54.5 mmol) of 5-chloro-2-methyl-phenyl isothiocyanate and 5.39 g (55 mmol) of 4-methyl-2-amino-oxazole to give 8.3 g of title compound as a yellow solid, m.p. 207–208° C. An additional crop (4.8 g, m.p. 207–208° C.) was obtained from the mother liquor (86% combined yield).

NMR (DMSO-$d_6$, 400 MHz): 2.133 (s, 3H, ArCH$_3$), 2.439 (m, 3H, ArCH$_3$), 7.26 (m, 3H, ArH), 7.38 (s, 2H, ArH+NH), 10.476 (s, 1H, NH). MS [EI, m/z]: 281 [M]$^+$, 266, 141 [b.p.]; Anal. Calc'd. for $C_{12}H_{12}ClN_3OS$ : C, 51.15; H, 4.29; N, 14.91 Found: C, 50.86; H, 4.10; N, 14.91.

EXAMPLE 5

1-(5-Chloro-2-methyl-phenyl)-3-(5-methyl-[1,3,4]thiadiazol-2-yl)-thiourea

Prepared using Method D from 4.5 g (24.5 mmol) of 5-chloro-2-methyl-phenyl isothiocyanate and 2.82 g (24.5 mmol) of 5-amino-2-methyl-[1,3,4]thiadiazole to give 2.2 g of solids. Pure title compound was obtained by trituration of the crude solid with 1N HCl. The solids were collected, washed with $H_2O$, EtOAc and dried under high vacuum to give 2.1 g of the title compound as a white solid (29% yield, m.p. sinters 190° C., melts >250° C.).

NMR (DMSO-$d_6$, 400 MHz): 2.15 (s, 3H, ArCH$_3$), 2.47 (s, 3H, ArCH3), 7.20 (d, 1H, ArH), 7.26 (d, 1H, ArH), 7.36 (broad s, 1H, ArH), 10.02 (s, 1H, NH), 13.75 (broad, 1H, NH). MS [EI, m/z]: 298 [M]$^+$, 265, 115 [b.p.].

EXAMPLE 6

1-(5-Chloro-2-methyl-phenyl)-3-(1-methyl-1H-pyrazol-3-yl)-thiourea

Prepared using Method A from 4.73 g (27.5 mmol) of 5-chloro-2-methyl-phenyl isothiocyanate and 2.5 g (25.7 mmol) of 1-methyl-3-aminopyrazole to give 6.8 g of title compound as a white solid (95% yield, m.p. 217–218° C.)

NMR (DMSO-$d_6$, 400 MHz): 2.25 (s, 3H, ArCH$_3$), 3.78 (m, 3H, ArCH$_3$), 5.975 (s, 1H, ArH), 7.195 (dd, 1H, ArH), 7.28 (d, 1H, ArH), 7.66 (d, 1H, ArH), 7.955 (d, 1H, ArH), 10.8 (s, 1H, NH), 11.35 (broad, 1H, NH). MS [EI, m/z]: 280 [M]$^+$, 265, 247,197, 97 [b.p.]; Anal. Calc'd. for $C_{12}H_{13}ClN_4S$ : C, 51.33; H, 4.67; N, 19.95 Found: C, 51.13; H, 4.51; N, 19.95.

EXAMPLE 7

1-(5-Chloro-2-methyl-phenyl)-3-(1H-pyrazol-3-yl)-thiourea

Prepared using Method A from 5.5 g (30.1 mmol) of 5-chloro-2-methyl-phenyl isothiocyanate and 2.5 g (30.1 mmol) of 3-amino-1H-pyrazole to give 5.3 g of tite compound as a white solid (66% yield, m.p. 221–222° C.).

NMR (DMSO-$d_6$, 400 MHz): (major tautomer): 2.235 (s, 3H, ArCH$_3$), 6.01 (s, 1H, ArH), 7.20 (d, 1H, ArH), 7.28 (d, 1H, ArH), 7.72 (s, 1H, ArH), 7.91 (s, 1H, ArH), 10.84 (s, 1H, NH), 11.5 (broad, 1H, NH), 12.66 (s, 1H, NH). (minor tautomer): 2.16 (s, 3H, ArCH$_3$), 5.68 (s, 1H, ArH), 5.95 (d, 1H, ArH), 7.28 (d, 1H, ArH), 7.41 (d, 1H, ArH), 8.36 (d, 1H, ArH), 10.79 (s, 1H, NH), 11.5 (broad, 1H, NH), 12.66 (s, 1H, NH). MS [EI, m/z]: 266 [M]$^+$, 251, 233,183, 83 [b.p.]; Anal. Calc'd. for C$_{11}$H$_{11}$ClN$_4$S: C, 49.63; H, 4.16; N, 21.00 Found: C, 49.55; H, 4.06; N, 21.20.

EXAMPLE 8

1-(5-Chloro-2-methyl-phenyl)-3-(1,3,5-trimethyl-1H-pyrazol-4-yl)-thiourea

Prepared using Method A from 4.5 g (24.5 mmol) of 5-chloro-2-methyl-phenyl isothiocyanate and 3.06 g (24.5 mmol) of 4-amino-1,3,5-trimethylpyrazole to give 5.4 g of title compound as a white solid, m.p. 176–177° C. (71% yield).

NMR (DMSO-$d_6$, 400 MHz): 2.02 (s, 3H, ArCH$_3$), 2.094 (broad s, 6H, ArCH$_3$), 3.61 (s, 3H, NCH$_3$), 7.05 (broad s, 1H, ArH), 7.08 (s, 2H, ArH), 8.57 (broad, 1H, NH), 9.14 (broad, 1H, NH). MS [EI, m/z]: 308 [M$^+$, b.p.], 275, 167, 142, 125. Anal. Calc'd. for C$_{14}$H$_{17}$ClN$_4$S: C, 54.45; H, 5.55; N, 18.14 Found: C, 54.23; H, 5.58; N, 18.06.

EXAMPLE 9

1-(5-Chloro-2-methyl-phenyl)-3-(4-methyl-thiazol-2-yl)-thiourea

Prepared using Method B from 4.5 g (24.5 mmol) of 5-chloro-2-methyl-phenyl isothiocyanate and 2.8 g (24.5 mmol) of 2-amino4-methylthiazole to give 4.8 g of title compound as an off- white solid (95% yield, m.p. 188° C.).

NMR (DMSO-$d_6$, 400 MHz): 2.19 (s, 6H, ArCH3), 6.58 (broad, 1H, ArH), 7.18 (dd, 1H, ArH), 7.26 (d, 1H, ArH), 7.605 (broad, 1H, ArH), 10.0 (very broad 1H, NH), 12.24 (broad, 1H, NH). MS [EI, m/z]: 297 [M]$^+$, 114 [b.p.]; Anal. Calc'd. for C$_{12}$H$_{12}$ClN$_3$S$_2$: C, 48.39; H, 4.06; N, 14.11 Found: C, 48.18; H, 3.88; N, 14.08.

EXAMPLE 10

1-(5-Chloro-2-methyl-phenyl)-3-(4,5-dimethyl-thiazol-2-yl)-thiourea

Prepared using Method B from 4.5 g (24.5 mmol) of 5-chloro-2-methyl-phenyl isothiocyanate and 2.79 g (24.5 mmol) of 2-amino-4,5-dimethylthiazole to give 2.4 g of title compound as a white solid (31% yield, m.p. 188–189° C.).

NMR (DMSO-$d_6$, 400 MHz): 2.092 (s, 3H, ArCH$_3$), 2.15 (s, 3H, ArCH$_3$), 2.17 (s, 3H, ArCH$_3$), 7.16 (dd, 1H, ArH), 7.24 (d, 1H, ArH), 7.15 (broad, 1H, ArH), 9.5 (broad, 1H, NH), 12.13 (broad, 1H, NH). MS [EI, m/z]: 311 [M]$^+$, 171, 128 [b.p.]; Anal. Calc'd. for C$_{13}$H$_{14}$ClN$_3$S$_2$: C, 50.07; H, 4.53; N, 13.47 Found: C, 49.70; H, 4.32; N, 13.45.

EXAMPLE 11

{2-[3-(5-Chloro-2-methyl-phenyl)-thioureido]-thiazol-4-yl }-acetic Acid Ethyl Ester Prepared using Method B from 4.5 g (24.5 mmol) of 5-chloro-2-methyl-phenyl isothiocyanate and 4.56 g (24.5 mmol) of 2-(2-amino-thiazol-4-yl)-acetic acid ethyl ester to give 3.62 g of title compound as a white solid (40% yield, m.p. 177–179° C.).

NMR (DMSO-$d_6$, 400 MHz): 1.53 (t, 3H, OCH$_2$CH$_3$), 2.191 (s, 3H, ArCH$_3$), 3.691 (s, 2H, CH$_2$CO), 4.06 (q, 2H, OCH$_2$CH$_3$), 6.92 (broad, 1H, ArH), 7.21 (dd, 1H, ArH), 7.28 (d, 1H, ArH), 7.74 (broad, 1H, ArH), 9.5 (broad, 1H, NH), 12.1 (broad, 1H, NH). MS [EI, m/z]: 369 [M]$^+$, 186 [b.p.]; Anal. Calc'd. for C$_{15}$H$_{16}$ClN$_3$O$_2$S$_2$: C, 48.71; H, 4.36; N, 11.36 Found: C, 48.59; H, 4.45; N, 11.30.

EXAMPLE 12

1-(5-Chloro-2-methyl-phenyl)-3-(3-methyl-isothiazol-5-yl)-thiourea

Prepared using Method B from 4.5 g (24.5 mmol) of 5-chloro-2-methyl-phenyl isothiocyanate and 2.8 g (24.5 mmol) of 5-amino-2-methylisothiazole to give 3.3 g of title compound as an off- white solid (45% yield, m.p. 187–188° C. with decomposition).

NMR (DMSO-$d_6$, 400 MHz): 2.17 (s, 3H, ArCH$_3$), 2.28 (s, 3H, ArCH$_3$), 6.82 (s, 1H, ArH), 7.26 (m, 2H, ArH), 7.445 (d, 1H, ArH), 9.72 (broad s, 1H, NH), 11.59 (broad, 1H, NH). MS [EI, m/z]: 297 [M]$^+$, 263, 256, 215, 184, 151, 114 [b.p.]; Anal. Calc'd. for C$_{12}$H$_{12}$ClN$_3$S$_2$: C, 48.39; H, 4.06; N, 14.11 Found: C, 48.06; H, 4.03; N, 13.94.

EXAMPLE 13

1-(5- Chloro-2-methyl-phenyl)-3-(2-methyl-benzothiazol-5-yl)-thiourea

Prepared using Method A from 4.5 g (24.5 mmol) of 5-chloro-2-methyl-phenyl isothiocyanate and 4.02 g (24.5 mmol) of 5-amino-2-methylbenzothiazole to give 6.0 g of crude material. Soxhlet extraction with EtOAc gave 2.5 g of pure title compound as a tan solid (29% yield, m.p. 173–174° C. ).

NMR (DMSO-$d_6$, 400 MHz): 2.22 (s, 3H, ArCH$_3$), 2.781 (s, 3H, ArCH$_3$), 7.21 (dd, 1H, ArH), 7.26 (d, 1H, ArH), 7.385 (s, 1H, ArH), 7.43 (m, 1H, ArH), 7.95 (d, 1H, ArH), 8.05 (d, 1H, ArH), 9.439 (s, 1H, NH), 10.002 (s, 1H, NH). MS [EI, m/z]: 347 [M]$^+$, 313 [b.p.]; Anal. Calc'd. for C$_{16}$H$_{14}$ClN$_3$S$_2$+0.03 mol EtOAc : C, 55.24; H, 4.09; N, 11.99 Found: C, 55.11; H, 4.00; N, 11.92.

EXAMPLE 14

1-(5-Chloro-2-methyl-phenyl)-3-(5-ethyl-[1,3,4] thiadiazol-2-yl)-thiourea

Prepared using Method D from 4.5 g (24.5 mmol) of 5-chloro-2-methyl-phenyl isothiocyanate and 3.16 g (24.5 mmol) of 5-amino-2-ethyl-[1,3,4]thiadiazole to give 3.0 g of residual solids. Pure title compound was obtained by trituration of the crude solid with 1N HCl. The solids were collected, washed with H$_2$O, EtOAc and dried under high vacuum to give 2.55 g of the title compound as a white solid (34% yield, m.p. sinters 170° C., melts 231–233° C. with decomposition).

NMR (DMSO-$d_6$, 400 MHz): 1.24 (t, 3H, CH2CH$_3$), 2.152 (s, 3H, ArCH$_3$), 2.84 (q, 2H, CH$_2$CH$_3$), 7.20 (dd, 1H, ArH), 7.26 (d, 1H, ArH), 7.34 (s, 1H, ArH), 10.04 (s, 1H, NH), 13.5 (broad, 1H, NH). MS [EI, m/z]: 312 [M]$^+$, 279, 129 [b.p.]; Anal. Calc'd. for C$_{12}$H$_{13}$ClN$_4$S$_2$: C, 46.07; H, 4.19; N, 17.19 Found: C, 46.21; H, 4.13; N, 17.99.

EXAMPLE 15

1-(2-Chloro-6-methyl-phenyl)-3-(1,3,5-trimethyl-1H-pyrazol-4-yl)-thiourea

Prepared using Method A from 4.0 g (21.8 mmol) of 2-chloro-6-methyl-phenyl isothiocyanate and 2.7 g (21.8 mmol) of 4-amino-1,3,5-trimethylpyrazole to give 4.5 g of title compound as a white solid (67% yield, m.p. 201–202° C.).

NMR (DMSO-d$_6$, 400 MHz): 2.05 (broad s, 3H, ArCH$_3$), 2.12 (broad s, 3H, ArCH$_3$), 2.16 (broad s, 3H, ArCH$_3$), 3.61 (s, 3H, NCH$_3$), 7.16 (broad s, 2H, ArH), 7.27 (broad s, 1H, ArH), 8.44 (broad, 1H, NH), 9.13 (broad, 1H, NH). MS [EI, m/z]: 308 [M]$^+$, 273 [b.p.]; Anal. Calc'd. for C$_{14}$H$_{17}$ClN$_4$S: C, 54.45; H, 5.55; N, 18.14 Found: C, 54.25; H, 5.30; N, 17.92.

EXAMPLE 16

1-(4-Chloro-2-methyl-phenyl)-3-(1,3,5-trimethyl-1H-pyrazol-4-yl)-thiourea 0.12 Solvate with Acetic Acid Ethyl Ester Prepared using Method A from 4.0 g (21.8 mmol) of 4-chloro-2-methyl-phenyl isothiocyanate and 2.7 g (21.8 mmol) of 4-amino-1,3,5-trimethylpyrazole to give 5.5 g of title compound as a white solid (82% yield, m.p. 178° C.).

NMR (DMSO-d$_6$, 400 MHz): 2.02 (broad s, 3H, ArCH$_3$), 2.08 (broad s, 3H, ArCH$_3$), 2.11 (broad s, 3H, ArCH$_3$), 3.32 (s, 3H, NCH$_3$), 7.02 (broad s, 1H, ArH), 7.19 (s, 1H, ArH), 7.27 (broad s, 1H ArH), 8.52 (broad, 1H, NH), 9.13 (broad, 1H, NH). MS [EI, m/z]: 308 [M$^+$, b.p.], 275. Anal. Calc'd. for C$_{14}$H$_{17}$ClN$_4$S+0.12 mol EtOAc: C, 54.45; H, 5.65; N, 17.64 Found: C, 54.32; H, 5.52; N, 17.62.

EXAMPLE 17

1-(4-Chloro-2-methyl-phenyl)-3-(4-methyl-oxazol-2-yl)-thiourea

Prepared using Method A from 4.04 g (22 mmol) of 4-chloro-2-methyl-phenyl isothiocyanate and 2.16 g (22 mmol) of 2-amino-4-methyloxazole to give 4.5 g of crude title compound. Pure title compound was obtained by flash chromatography (silica Merck 60, CH$_2$Cl$_2$-CH$_3$OH, 19:1) and crystallization from CH$_3$CN to give 2.12 g of the title compound as a yellow solid (72.5% yield, m.p. 214° C. with decomposition).

NMR (DMSO-d$_6$, 400 MHz): 2.14 (s, 3H, ArCH$_3$), 2.43 (s, 3H, ArCH$_3$), 7.17 (d, 1H, ArH), 7.26 (dd, 1H, ArH), 7.36 (m, 3H, ArH+NH), 10.45 (s, 1H, NH). MS [EI, m/z]: 281 [M]$^+$, 256, 248, 141 [b.p.]; Anal. Calc'd. for C$_{12}$H$_{12}$ClN$_3$OS: C, 51.15; H, 4.29; N, 14.91 Found: C, 50.87; H, 4.10; N, 14.76.

EXAMPLE 18

1-(2-Chloro-6-methyl-phenyl)-3-(4-methyl-oxazol-2-yl)-thiourea

Prepared using Method A from 4.04 g (22 mmol) of 2-chloro-6-methyl-phenyl isothiocyanate and 2.16 g (22 mmol) of 2-amino4-methyloxazole to give 2.4 g of an amber oil. Crystallization from CH$_3$CN afforded 2.4 g of the title compound as a yellow solid (39% yield, m.p. 222° C. with decomposition).

NMR (DMSO-d$_6$, 400 MHz): 2.167 (s, 3H, ArCH$_3$), 2.434 (s, 3H, ArCH$_3$), 7.239 (m, 2H, ArH), 7.32–7.4 (m, 3H, ArH+NH), 10.4 (s, 1H, NH). MS [+FAB, m/z]: 282 [M+H]$^+$.

EXAMPLE 19

3-(5-Chloro-2-methyl-phenyl)-1-ethyl-1-(1,3,5-trimethyl-1H-pyrazol-4-yl)-thiourea Step A: 4-Acetamido-1,3,5-trimethyl-1H-pyrazole Under anhydrous conditions, a mixture of 4-amino-1,3,5-trimethyl-1H-pyrazole (10 g, 80 mmol) and triethylamine (16.7 mL, 120 mmol) was treated dropwise with acetyl chloride (6.3 mL, 88 mmol). The reaction mixture was stirred at ambient temperature for 72 hours. The triethylamine hydrochloride was removed by vacuum filtration. The filtrate was concentrated in vacuo and the residue triturated with Et$_2$O to give 9.6 g of title compound as a tan solid (72% yield, m.p. 118–119° C.).

NMR (DMSO-d$_6$, 400 MHz): 1.916 (s, 3H, COCH$_3$), 1.9446 (s, 3H, ArCH$_3$), 2.003 (s, 3H, ArCH$_3$), 3.5879 (s, 3H, NCH$_3$) MS (EI, m/z): 167 [M]$^+$.

Step B: 4-Ethylamino-1,3,5-trimethyl-1H-pyrazole

Under an atmosphere of nitrogen, lithium aluminum hydride, LAH, (4.3 g, 113.6 mmol) was added portionwise to a vigorously stirred solution of 4-acetamido-1,3,5-trimethyl-1H-pyrazole (9.5 g, 56.8 mmol) of step A. After stirring at ambient temperature for 2 hours, the mixture was heated at reflux for 1 hour and the excess LAH was decomposed by the careful addition of 4.3 mL of H$_2$O, 4.3 mL of 1N NaOH, 12.9 mL of H$_2$O and 54 g Na$_2$SO$_4$. The solids were filtered and the filtrate concentrated in vacuo to give 7.26 g of title compound as a brown oil (91% crude yield).

NMR (DMSO-d$_6$, 400 MHz): 0.97 (t, 3H, CH$_2$CH$_3$), 1.98 (s, 3H, ArCH$_3$), 2.06 (s, 3H, ArCH$_3$), 2.72 (q, 2H, CH$_2$CH$_3$), 3.536 (s, 3H, NCH$_3$); MS (EI, m/z): 153 [M]$^+$.

Step C: 3-(5-Chloro-2-methyl-phenyl)-1-ethyl-1-(1,3,5-trimethyl-1H-pyrazol-4-yl)-thiourea Prepared using Method A from 9.33 g (51 mmol) of 5-chloro-2-methyl-phenyl isothiocyanate and 4-ethylamino-1,3,5-trimethylpyrazole (7.2 g, 47 mmol) of step B to give 5.4 g of title compound as a white solid (70% yield, m.p. 144–145° C.).

NMR (DMSO-d$_6$, 400 MHz): 1.07 (t, 3H, CH$_2$CH$_3$), 2.04 (s, 3H, ArCH$_3$), 2.07 (s, 3H, ArCH$_3$), 2.11 (s, 3H, ArCH$_3$), 3.82 (s, 3H, NCH$_3$), 4.23 (m, 2H, CH$_2$CH$_3$), 7.02 (s, 1H, ArH), 7.19 (s, 2H, ArH), 8.41 (s, 1H, NH). MS [EI, m/z]: 336 [M]$^+$, 195 [b.p.]; Anal. Calc'd. for C$_{16}$H$_{21}$ClN$_4$S: C, 57.04; H, 6.28; N, 16.63 Found: C, 56.93; H, 6.18; N, 16.44.

The substituted 1-aryl-3-heteroaryl isothioureas of Examples 20–21 were prepared as follows:

EXAMPLE 20

(E)-1-(5-Chloro-2-methyl-phenyl)-2-methyl-3-(1,3,5-trimethyl-1H-pyrazol-4-yl)-isothiourea Under anhydrous conditions, a solution of 1-(5-Chloro-2-methyl-phenyl)-3-(1,3,5-trimethyl-1H-pyrazol-4-yl)-thiourea (2.3 g, 7.5 mmol) produced in example 8 and methyl iodide (0.94 mL, 15 mmol) in 70 mL of acetone was stirred at ambient temperature for 64 hours. The reaction mixture was concentrated in vacuo and partitioned between CH$_2$Cl$_2$ and saturated aqueous NaHCO$_3$ solution. The organic phase was washed with dilute Na$_2$S$_2$O$_3$ and dried (Na$_2$SO$_4$). Removal of solvent and crystallization of the residue from Et$_2$O provided 1.78 g of title compound as a white solid (74% of theory, m.p. 134–135° C.).

NMR (DMSO-d$_6$, 400 MHz): 1.97 (s, 3H, ArCH$_3$), 2.03 (s, 3H, ArCH$_3$), 2.06 (s, 3H, ArCH$_3$), 2.29 (s, 3H, SCH$_3$), 3.60 (s, 3H, NCH$_3$), 6.678 (s, 1H, ArH), 6.87 (dd, 1H, ArH), 7.12 (d, 1H, ArH), 7.45 (s, 1H, NH). MS (+FAB, m/z): 323 [M+H]$^+$. Anal. Calc'd for C$_{15}$H$_{19}$ClN$_4$S: C, 55.80; H, 5.93; N, 17.35 Found: C, 55.70; H, 5.88; N, 17.36.

EXAMPLE 21

3-(5-Chloro-2-methyl-phenyl)-1-ethyl-2-methyl-1-(1,3,5-trimethyl-1H-pyrazol-4-yl)-isothiourea 1:1 Salt with Hydrochloric Acid A mixture of 3-(5-Chloro-2-methyl-phenyl)-1-ethyl-1-(1,3,5-trimethyl-1H-pyrazol-4-yl)-thiourea (6.2 g, 19.1 mmol)

of example 19, methyl iodide (2.4 mL, 38.3 mmol), and potassium carbonate (5.24 g, 38 mmol) in 100 mL of acetone was heated at reflux for 7 hours. The solids were filtered washed with EtOAc and the filtrate concentrated in vacuo. The removal of solvent in vacuo provided the title compound as a clear oil (6.2 g, 92% of theory). The hydrochloride salt was prepared by treating an ethereal solution of the title compound with 20 mL of 1N HCl in Et$_2$O. The salt was filtered and dried under high vacuum to provide the title compound as a white solid (3.2 g, 43% of theory, m.p. 158° C. with decomposition).

NMR (DMSO-d$_6$, 400 MHz): 1.102 (t, 3H, CH$_2$CH$_3$), 1.9 (s, 3H, ArCH$_3$), 2.03 (broad s, 3H, ArCH$_3$), 2.118 (broad s, 3H, ArCH$_3$), 2.16 (s, 3H, SCH$_3$), 3.619 (broad s, 3H, NCH$_3$), 3.79 (broad, 2H, CH$_2$CH$_3$), 7.12 (broad, 2H, ArH), 7.22 (d, 1H, ArH). MS [EI, m/z]: 350 [M]$^+$, 152 [b.p.]; Anal. Calc'd. for C$_{17}$H$_{23}$ClN$_4$S.HCl: C, 52.71; H, 6.24; N, 14.46 Found: C, 52.46; H, 6.16; N, 14.53.

The present invention may be embodied in other specific forms without departing from the spirit and essential attributes thereof and accordingly, reference should be made to the appended claims, rather than to the foregoing specification, as indicating the scope of the invention.

What is claimed is:

1. A method of treating atherosclerosis mammals in need thereof, which comprises administering to said mammal an anti-atherosclerotic effective amount of a compound represented by Formulas I and II:

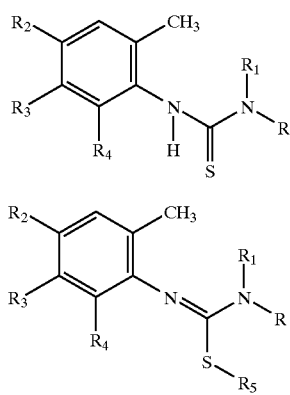

wherein

R is

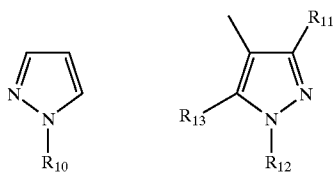

wherein R$_{10}$, R$_{11}$, R$_{12}$, and R$_{13}$ are each, independently, hydrogen or a lower alkyl of 1–6 carbon atoms;

R$_1$ is hydrogen or a lower alkyl of 1–6 carbon atoms;

R$_2$, R$_3$, and R$_4$ are each, independently, hydrogen or halogen; and

R$_5$ is a lower alkyl of 1–6 carbon atoms;

or a pharmaceutically acceptable salt thereof.

2. The method of claim 1, wherein said compound is 1-(5-chloro-2-methyl-phenyl)-3-(1-methyl-1H-pyrazol-3-yl)-thiourea.

3. The method of claim 1, wherein said compound is 1-(5-chloro-2-methyl-phenyl)-3-(1H-pyrazol-3-yl)-thiourea.

4. The method of claim 1, wherein said compound is 1-(5-chloro-2-methyl-phenyl)-3-(1,3,5-trimethyl-1H-pyrazol-4-yl)-thiourea.

5. The method of claim 1, wherein said compound is 1-(2-chloro-6-methyl-phenyl)-3-(1,3,5-trimethyl-1H-pyrazol-4-yl)-thiourea.

6. The method of claim 1, wherein said compound is 1-(4-chloro-2-methyl-phenyl)-3-(1,3,5-trimethyl-1H-pyrazol-4-yl)-thiourea.

7. The method of claim 1, wherein said compound is 3-(5-chloro-2-methyl-phenyl)-1-ethyl-1-(1,3,5-trimethyl-1H-pyrazol-4-yl)-thiourea.

8. The method of claim 1, wherein said compound is (E)-1-(5-chloro-2-methyl-phenyl)-2-methyl-3-(1,3,5-trimethyl-1H-pyrazol-4-yl)-isothiourea.

9. The method of claim 1, wherein said compound is 3-(5-chloro-2-methyl-phenyl)-1-ethyl-2-methyl-1-(1,3,5-trimethyl-1H-pyrazol-4-yl)-isothiourea.

* * * * *